(12) United States Patent
Zimmerle et al.

(10) Patent No.: US 11,262,350 B2
(45) Date of Patent: Mar. 1, 2022

(54) DETECTION OF ASCORBIC ACID IN A URINE SAMPLE

(71) Applicant: Siemens Healthcare Diagnostics Inc., Tarrytown, NY (US)

(72) Inventors: Chris Zimmerle, Goshen, IN (US); Gary Rheinheimer, Goshen, IN (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 386 days.

(21) Appl. No.: 16/344,152

(22) PCT Filed: Oct. 27, 2017

(86) PCT No.: PCT/US2017/058659
§ 371 (c)(1),
(2) Date: Apr. 23, 2019

(87) PCT Pub. No.: WO2018/081496
PCT Pub. Date: May 3, 2018

(65) Prior Publication Data
US 2021/0311026 A1 Oct. 7, 2021

Related U.S. Application Data

(60) Provisional application No. 62/414,176, filed on Oct. 28, 2016.

(51) Int. Cl.
| | | |
|---|---|---|
| G01N 33/52 | (2006.01) | |
| G01N 33/82 | (2006.01) | |
| G01N 21/78 | (2006.01) | |
| G01N 31/22 | (2006.01) | |
| G01N 33/493 | (2006.01) | |

(52) U.S. Cl.
CPC .......... *G01N 33/521* (2013.01); *G01N 21/78* (2013.01); *G01N 31/22* (2013.01); *G01N 33/82* (2013.01); *G01N 33/493* (2013.01); *G01N 33/52* (2013.01); *G01N 33/523* (2013.01); *Y10T 436/142222* (2015.01)

(58) Field of Classification Search
CPC ...... G01N 21/77; G01N 21/78; G01N 33/493; G01N 33/52; G01N 33/521; G01N 33/523; G01N 33/82; G01N 31/22; Y10T 436/142222; Y10T 436/203332

USPC ........ 422/400–403, 420, 82.05; 436/93, 131, 436/164, 169
See application file for complete search history.

(56) References Cited

U.S. PATENT DOCUMENTS

| | | | | |
|---|---|---|---|---|
| 4,141,688 | A | | 2/1979 | Morris et al. |
| 4,152,116 | A | * | 5/1979 | Deneke ..................... C12Q 1/26 436/93 |
| 4,300,905 | A | * | 11/1981 | Bleisteiner ............. G01N 33/14 436/20 |
| 4,303,409 | A | * | 12/1981 | Ogawa .................... G01N 33/82 422/420 |
| 4,310,626 | A | * | 1/1982 | Burkhardt ................ C12Q 1/28 435/188 |
| 4,460,684 | A | * | 7/1984 | Bauer ...................... C12Q 1/28 435/14 |
| 4,587,220 | A | * | 5/1986 | Mayambala-Mwanika ................. C12Q 1/28 436/66 |
| 5,079,140 | A | | 1/1992 | Albarella et al. |
| 5,196,302 | A | | 3/1993 | Kidwell |
| 5,264,348 | A | | 11/1993 | Schick et al. |
| 5,945,345 | A | * | 8/1999 | Blatt ................ G01N 33/54366 436/518 |
| 2007/0074971 | A1 | | 4/2007 | Atkinson et al. |

FOREIGN PATENT DOCUMENTS

| | | |
|---|---|---|
| JP | S481120 U | 1/1973 |
| JP | S5430890 A | 3/1979 |
| JP | H05184392 A | 7/1993 |
| JP | H0743239 U | 8/1995 |
| JP | H11304804 A | 11/1999 |

OTHER PUBLICATIONS

European Search Report and Search Opinion of European Application No. 17865511.4 dated Sep. 25, 2019.
International Search Report and Written Opinion of International Application No. PCT/US2017/058659 dated Jan. 5, 2018.

* cited by examiner

*Primary Examiner* — Maureen Wallenhorst

(57) ABSTRACT

Disclosed herein are methods of detecting ascorbic acid in a urine sample from a subject, including contacting at least a portion of the urine sample with a test strip including a reagent pad and detecting whether ascorbic acid is present in the urine sample by measuring an intensity of color on the reagent pad, wherein a reduction in the intensity of color on the reagent pad indicates the presence of ascorbic acid.

13 Claims, 6 Drawing Sheets

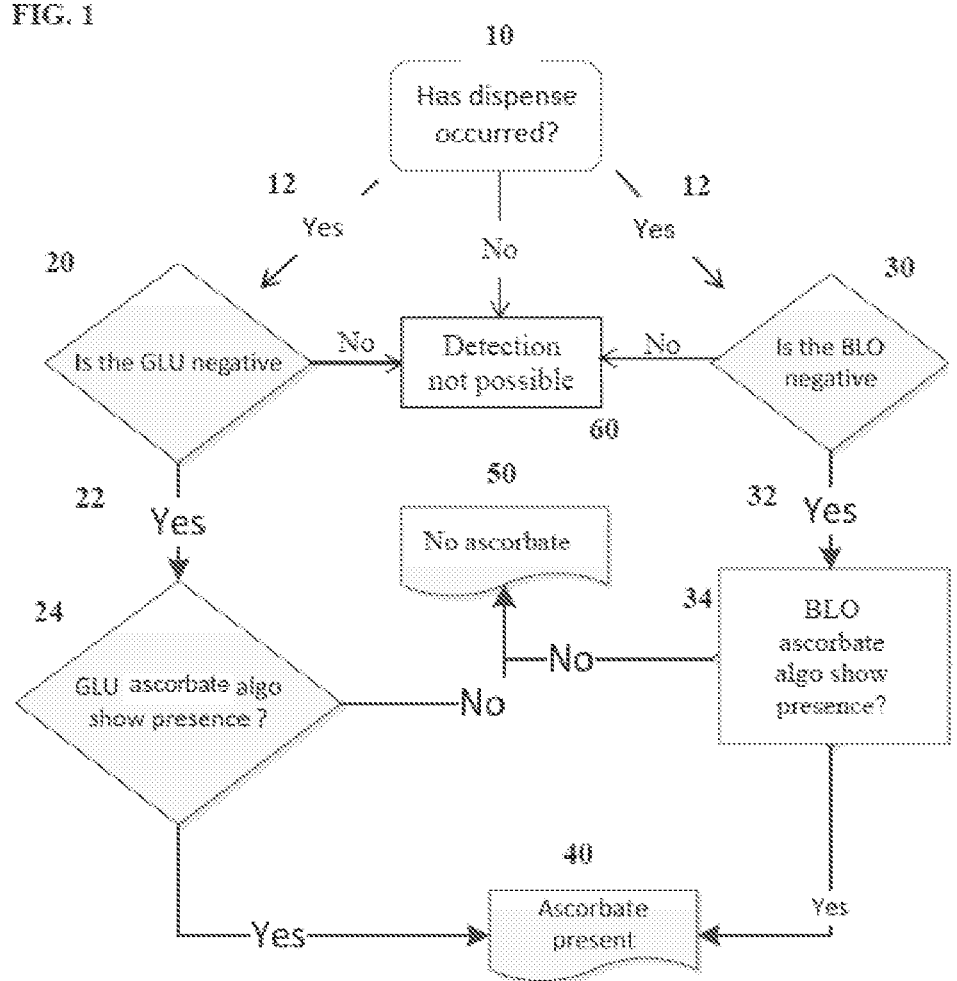

DETECTION OF ASCORBIC ACID IN A URINE SAMPLE

CROSS REFERENCE TO RELATED APPLICATIONS

This application claims priority to U.S. Provisional Application No. 62/414,176, filed Oct. 28, 2016, the disclosure of which is hereby incorporated by reference in its entirety.

TECHNICAL FIELD

Disclosed herein are methods of detecting ascorbic acid in a urine sample from a subject. Specifically, the disclosed methods provide an unconventional and non-routine way of detecting ascorbic acid in a urine sample using test strips containing reagent pads that are reactive with analytes such as glucose, blood, or both.

BACKGROUND

Reagent test strips are widely used in the field of clinical chemistry to detect the presence or absence of one or more constituents or one or more properties of interest in a patient sample, such as a urine sample. The test strip usually has one or more test areas ("reagent pads") that are capable of undergoing a color change in response to contact with the patient sample. The presence and/or concentration of the constituents or properties of interest in the patient sample can be determined by an analysis of the color changes that occurs on the reagent pad. Usually this analysis involves a color comparison between the reagent pad and a color standard or scale. In this way, reagent test strips assist physicians in diagnosing the existence of diseases and other health problems.

Ascorbic acid is often present in urine as a result of the use of vitamin C supplements or the intake of some citrus fruit. Ascorbic acid, however, can interfere with urinalysis assays by creating false negatives on certain reagent pads. For example, the urine sample may be positive for glucose, but the presence of ascorbic acid in the sample reduces the reagent signal on the glucose reagent pad resulting in a negative glucose reading (i.e. false negative) or a reduced glucose reading.

To prevent false negatives caused by the presence of ascorbic acid in urine samples, the reagent chemistry on the reagent pads (the glucose pad, for example) can be altered in such a way to add resistance to the effects of ascorbic acid. Alternatively, reagent pads specific for ascorbic acid can be added to the test strip, or an additional test strip having a reagent pad specific for ascorbic acid can be used. The addition of an ascorbic acid reagent pad to the test strip is not always possible, however, as there is often limited space available on the test strip. Additional test strips may not be desirable due to limited space in the analysis machine.

SUMMARY

Disclosed herein are methods of detecting ascorbic acid in a urine sample from a subject, comprising: contacting at least a portion of the urine sample with a test strip comprising a reagent pad, and detecting whether ascorbic acid is present in the urine sample by measuring an intensity of color on the reagent pad, wherein a reduction in the intensity of color on the reagent pad indicates the presence of ascorbic acid. In the disclosed methods, the reagent pad is not an ascorbic acid reagent pad.

Also provided are methods of detecting ascorbic acid in a urine sample with a test strip comprising a reagent pad, the method comprising: measuring, with electronics of an optical inspection apparatus, a first intensity of color from the reagent pad; contacting the test strip with at least a portion of the urine sample; measuring, with electronics of an optical inspection apparatus, a second intensity of color from the reagent pad; and detecting ascorbic acid in the urine sample, the detecting comprising determining a change in the intensity of color between the first intensity of color from the reagent pad and the second intensity of color from the reagent pad, wherein a reduction in the intensity of color on the reagent pad indicates the presence of ascorbic acid.

In some embodiments of the disclosed methods, the test strip comprises a glucose reagent pad, and the methods are performed using the glucose reagent pad. In some embodiments of the disclosed methods, the test strip comprises a blood reagent pad, and the methods are performed using the blood reagent pad. In some embodiments of the disclosed methods, the test strip comprises a glucose reagent pad and a blood reagent pad, and the methods are performed using both the glucose reagent pad and the blood reagent pad.

BRIEF DESCRIPTION OF THE DRAWINGS

The summary, as well as the following detailed description, is further understood when read in conjunction with the appended drawings. For the purpose of illustrating the disclosed methods, there are shown in the drawings exemplary embodiments of the methods; however, the methods are not limited to the specific embodiments disclosed. In the drawings:

FIG. 1 illustrates an exemplary detection scheme for detecting ascorbic acid in the urine of a subject.

Unless otherwise noted, the figures contain box plots, wherein the horizontal line within the box corresponds to the median value (25 to 75% of the data), and the top and bottom of the boxes represent 5% to 95% of the data, respectively. * represent data outside these points—so called outliers.

Figure 6:
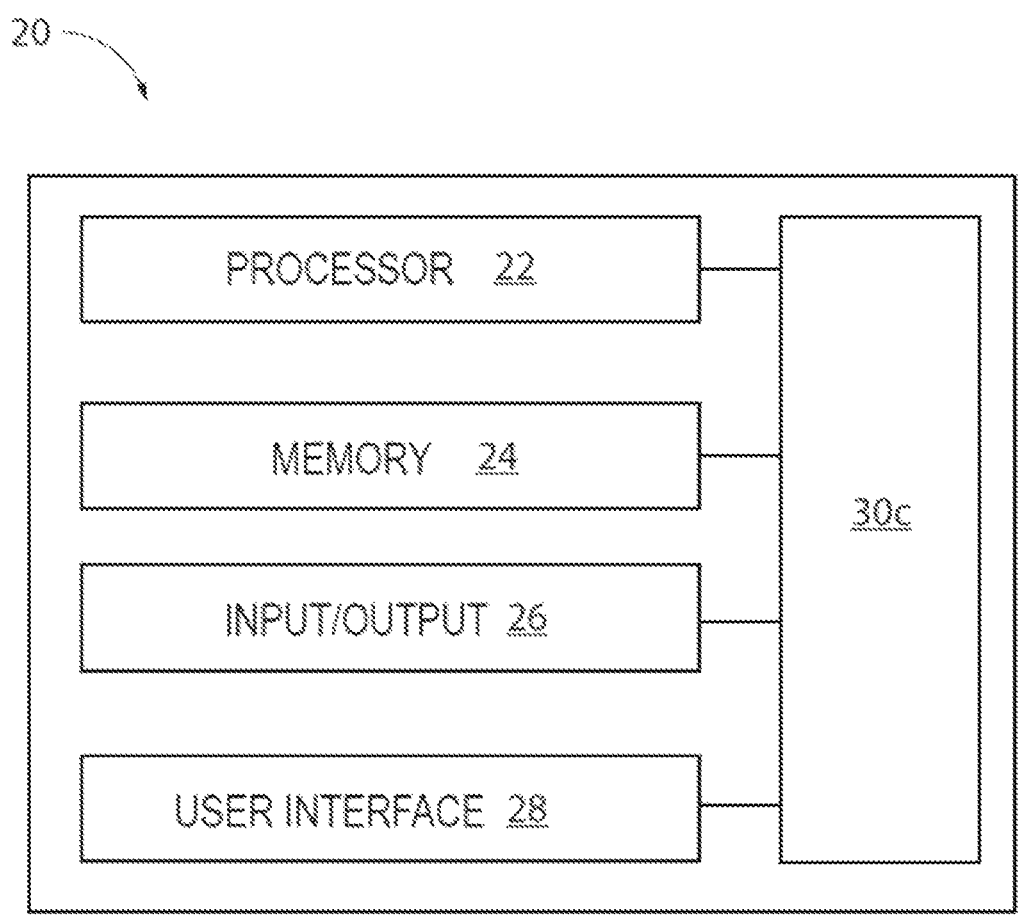

FIG. 6 illustrates an exemplary computing device in accordance with an embodiment of the present disclosure.

DETAILED DESCRIPTION OF ILLUSTRATIVE EMBODIMENTS

The disclosed methods may be understood more readily by reference to the following detailed description taken in connection with the accompanying figures, which form a part of this disclosure. It is to be understood that the disclosed methods are not limited to the specific methods described and/or shown herein, and that the terminology used herein is for the purpose of describing particular embodiments by way of example only and is not intended to be limiting of the claimed methods.

It is to be appreciated that certain features of the disclosed methods which are, for clarity, described herein in the context of separate embodiments, may also be provided in combination in a single embodiment. Conversely, various features of the disclosed methods that are, for brevity, described in the context of a single embodiment, may also be provided separately or in any subcombination.

As used herein, the singular forms "a," "an," and "the" include the plural.

Various terms relating to aspects of the description are used throughout the specification and claims. Such terms are to be given their ordinary meaning in the art unless otherwise indicated. Other specifically defined terms are to be construed in a manner consistent with the definitions provided herein.

"Ascorbic acid" and "ascorbate" are used interchangeably herein.

As used herein, "bleaching" refers to the process by which ascorbic acid: 1) prevents the reagent pad from undergoing a color change in the presence of an analyte, respectively, such that the color of the wet pad (post-urine application) is the same or comparable to the color of the dry pad (pre-urine application); or 2) causes the reagent pad to undergo a reduction in the intensity of color from that normally observed upon reaction of the pad with an analyte, respectively. "Reduction in the intensity of color" refers to a lighter change in color or a change in color to the opposite end of the RGB spectrum as normally observed upon contact with urine to the reagent pad.

The term "comprising" is intended to include examples encompassed by the terms "consisting essentially of" and "consisting of"; similarly, the term "consisting essentially of" is intended to include examples encompassed by the term "consisting of."

As used herein, the term "dispense decode" represents a measure of the full color change brought about by dispensing urine onto the reagent pad.

Conventional spectrophotometers may be used to perform a number of different urinalysis tests utilizing a test strip on which a number of different reagent pads are disposed. A conventional spectrophotometer determines the color of a urine sample disposed on a white/yellow, non-reactive pad. Each reagent pad is provided with a different reagent which causes a color change in response to the presence of a certain type of analyte in urine. By illuminating the pad and taking a number of reflectance readings from the pad, each having a magnitude relating to a different wavelength of visible light, the presence and/or concentration of the analyte of interest can be determined. Analytes of interest for urine include, for example, glucose and blood [leukocytes (white blood cells) and/or erythrocytes (red blood cells)]. After contacting the reagent pad with urine, the presence of the foregoing analytes of interest may then be determined based upon the relative magnitudes of red, green, and blue (RGB) reflectance signals. These reflectance signals can be obtained and quantified by an optical inspection apparatus (which is described in detail below). The analytes within the clinical samples change the reagent pad to the following colors: reagent pad for blood—toward dark green; reagent pad for glucose—toward dark red. The color developed as a result of the presence of a particular analyte defines the characteristic discrete spectrum for absorption of light for that particular analyte. For example, any glucose present in the urine reacts with the reagent on the glucose reagent pad, causing the reagent pad to change color to an extent which depends on the concentration of the glucose. The characteristic absorption spectrum for color-developed glucose falls within the upper end of the blue spectrum and the lower end of the green spectrum. Any blood present in the urine reacts with the reagent on the reagent pad, causing the reagent pad to change color to an extent which depends on the concentration of the blood. For example, in the presence of a relatively large concentration of blood, such a reagent pad may change in color from yellow toward dark green. Based upon the magnitude of the reflectance signal generated by the reflectance detector, the presence or absence of the analyte is determined. The presence of ascorbic acid in the urine, however, causes a "bleaching" effect on the reagent pad, resulting in a false negative (suggesting that no analyte is present in the urine) or a lower intensity color change (suggesting that the concentration of the analyte is lower than the actual concentration).

The disclosed ascorbic acid detection algorithms and methods of detecting ascorbic acid in a urine sample offer an advantage over existing methods by detecting ascorbic acid on reagent pads that are not ascorbic acid reagent pads. Examplary non-ascorbic acid reagent pads include glucose reagent pads, blood reagent pads, bilirubin reagent pads, ketone reagent pads, urobilinogen reagent pads, nitrite reagent pads, leukocyte esterase reagent pads, leukocyte reagent pads, albumin reagent pads, and/or creatinine reagent pads. Thus, the disclosed algorithms and methods enable the detection of ascorbic acid in a urine sample without the need to add an additional ascorbic acid-specific reagent pad to the test strip or an entirely separate test strip for the detection of ascorbic acid. The disclosed methods are unconventional and non-routine.

Ascorbic Acid Detection Algorithms

Disclosed herein is a series of algorithms for detecting ascorbic acid in a urine sample from a patient, using a reagent pad. As should be appreciated, these algorithms can be implemented on various optical inspection apparatuses, some of which are described in detail below.

In order to detect the presence of ascorbic acid, the urine sample is dispensed onto the reagent pad. Dispensing of urine onto the reagent pad can be determined using the dispense detection algorithm ("Dispense Detection Algorithm") provided in Formula I:

$$\text{Dispense Detection Algorithm} = (X - \text{dry(RGB)}) - IT(RGB)) + X \qquad \text{(Formula I)}$$

wherein X is an optional "offset" value which can be utilized to help filter out "noise" in the obtained RGB values. In some embodiments, X can equal 30. Thus, the Dispense Detection Algorithm can be presented as Formula Ia:

$$\text{Dispense Detection Algorithm} = (30 - \text{dry(RGB)}) - IT(RGB)) + 30 \qquad \text{(Formula Ia)}$$

The dry(RGB) value is the summation of the values across the RGB color system from the dry reagent pad (before contacting the reagent pad with urine). IT(RGB) is the summation of values across the RGB color system immediately after the reagent pad is contacted with urine. As used herein, "immediately after the reagent pad is contacted" means within the first 4 seconds after the urine is dispensed onto the reagent pad, and includes between about 0 seconds and about 4 seconds, between about 1 second and about 4 seconds, between about 2 seconds and about 4 seconds, or between about 3 seconds and about 4 seconds. "Immediately after the reagent pad is contacted" can be less than about 1 second, about 1 second, about 2 seconds, about 3 seconds, or about 4 seconds after urine is dispensed on the reagent pad. The Dispense Detection Algorithm is used to determine the reflectance value of the reagent pad after proper dispensing of urine onto the reagent pad has occurred but before a chemical reaction between the analyte and the reagent pad has had the opportunity to take place. Specific Dispense Detection Algorithm formulas for glucose and blood are presented in Formula Ib and Formula Ic, respectively, wherein Formula Ib represents the Dispense Detection Algorithm for a glucose reagent pad ("GLU Dispense Detection Algo") and Formula Ic represents the Dispense Detection Algorithm for a blood reagent pad ("BLO Dispense Detection Algo"):

GLU Dispense Detection Algorithm=$(X$-GLU·dry(RGB)-GLU·$IT$(RGB))+$X$   (Formula Ib)

BLO Dispense Detection Algorithm=$(X$-BLO·dry(RGB)-BLO·$IT$(RGB))+$X$   (Formula Ic)

wherein X is an optional "offset" value.

As discussed above, when sufficient quantities of ascorbic acid are present in the urine sample analyte measurements, such as glucose and blood measurements, can be adversely affected. In order to account for this effect, the reagent pad can be used to detect the presence of ascorbic acid by using the ascorbic acid algorithm ("Ascorbate Algorithm") provided in Formula II below:

Ascorbate Algorithm=(dispense decode)-(Dispense Detection Algo)   (Formula II)

wherein the dispense decode is the value across the RGB color system of the reagent pad at the maximum read time. Suitable maximum read times may depend on the specific reagents being used but illustrative maximum read times include about 30, 35, 40, 45, 50, 55, 60, or 65 seconds or more after the urine was dispensed on the reagent pad. The dispense decode is directly related to the concentration of analyte in the urine since reaction also results in an overall darkening of the strip. The Dispense Detection Algorithm is formula I (above).

Specific Ascorbate Algorithm formulas for glucose and blood are presented in Formula IIa and Formula IIb, respectively, wherein Formula IIa represents the Ascorbate Algorithm for a glucose reagent pad ("GLU Ascorbate Algo") and Formula IIb represents the Ascorbate Algorithm for a blood reagent pad ("BLO Ascorbate Algo"):

GLU Ascorbate Algorithm=(GLU dispense decode-GLU Dispense Detection Algo)   (Formula IIa)

BLO Ascorbate Algorithm=(BLO dispense decode-BLO Dispense Detection Algo)   (Formula IIb)

wherein the GLU Dispense Detection Algorithm or the BLO Dispense Detection Algorithm is subtracted from the GLU dispense decode or BLO dispense decode, respectively. The GLU dispense decode and BLO dispense decode represent the value across the RGB color system of the glucose reagent pad and blood reagent pad, respectively, at the maximum read time. The GLU dispense decode is directly related to the glucose concentration, while the BLO dispense decode is directly related to the blood concentration.

FIG. 1 illustrates an exemplary scheme for detecting ascorbic acid in the urine of a subject using a glucose reagent pad and/or blood reagent pad. Similar schemes can be used for detecting ascorbic acid in the urine of a subject using other reagent pads (including bilirubin reagent pads, ketone reagent pads, urobilinogen reagent pads, nitrite reagent pads, leukocyte esterase reagent pads, leukocyte reagent pads, albumin reagent pads, and/or creatinine reagent pads) and the following description of FIG. 1 is not intended to be limited to glucose reagent pads or blood reagent pads.

Referring to FIG. 1, urine is dispensed onto the glucose reagent pad and/or blood reagent pad. Dispensing of urine onto the reagent pads is verified at step 10. If the dispensing was not performed properly, no detection is possible 60.

If proper dispensing has occurred 12, the system determines if the glucose 20 and/or blood 30 are absent from the urine sample. The presence/absence of glucose and blood can be determined using an established glucose algorithm(s) ("GLU algorithm") and blood algorithm(s), respectively ("BLO algorithm"). The addition of urine to the glucose reagent pad and/or the blood reagent pad results in a rapid decrease in the reflectance on the reagent pad. If one or both of glucose 20 and blood 30 are not found in one or both of steps 20 or 30, the scheme in FIG. 1 can determine whether elevated levels of ascorbic acid are present in the sample 24, 34, which may have resulted in a false negative in one or both of steps 20 or 30. However, if glucose is found to be present 20, then detection of ascorbic acid based on the glucose pad is not possible 60. Likewise, in the event blood is found to be present 30, then detection of ascorbic acid based on the blood pad is not possible 60.

If glucose is determined to be absent from the sample 22, the glucose reagent pad can be used to test for the presence of ascorbic acid by measuring the level of reflectance from the glucose reagent pad 24 using the Ascorbate Algorithm of formula II, and more specifically the GLU Ascorbate Algorithm of Formula IIa. If the GLU Ascorbate Algorithm is less than the GLU Dispense Decode (i.e. less than the reflectance value obtained from a glucose reagent pad at the maximum read time after dispensing glucose onto the pad), then the GLU Ascorbate Algorithm indicates that ascorbic acid is present 40.

Under normal conditions (i.e., when ascorbic acid is either not present or only present in low concentrations) a glucose pad should show a predictable color change (over time) when exposed to a sample containing glucose—it will get darker in proportion to the level of glucose present. Illustrative glucose pads—once exposed to a sample containing glucose—will turn from blue-indigo color toward dark brown as the level of glucose in the sample increases. This is accomplished by the glucose in the sample reacting with compounds in the glucose reagent pad and producing a predictable color change. If, however, the color of the reagent pad doesn't change, then it is normally determined that no glucose was present in the sample. Elevated levels of ascorbic acid in the sample, however, lead to a "bleaching" effect on glucose reagent pads. In other words, if sufficient levels of ascorbic acid are present in the sample, the glucose reagent pad will not turn from a blue-indigo color toward dark brown as when glucose is present, but instead will either remain a blue-indigo color or turn from a blue-indigo color towards the white end of the spectrum. This lightening of the glucose reagent pad is an indication that while glucose may be present, the sample contains an elevated level of ascorbic acid that is masking the glucose reaction. If, however, the GLU Ascorbate Algorithm is greater than the GLU Dispense Decode, then the color of the reagent pad has gotten darker and the GLU Ascorbate Algorithm will not detect the presence of ascorbic acid and will therefore indicate that problematic levels of ascorbic acid is not present 50. It should be appreciated, however, that some amount of ascorbic acid is likely to be present in the sample, despite the GLU Ascorbate Algorithm being greater than the GLU Dispense Decode.

If blood is determined to be absent from the sample 32, the blood reagent pad can be used to test for the presence of ascorbic acid by measuring the level of reflectance from the blood reagent pad 34 using the Ascorbate Algorithm of formula II, and more specifically the BLO Ascorbate Algorithm of Formula IIb. If the BLO Ascorbate Algorithm is less than the BLO Dispense Decode (i.e. less than the reflectance value obtained from a blood reagent pad at the maximum read time after dispensing blood onto the pad), then the BLO Ascorbate Algorithm indicates that ascorbic acid is present 40.

Under normal conditions (i.e., when ascorbic acid is either not present or only present in low concentrations) a blood pad should show a predictable color change (over time) when exposed to a sample containing blood—it will get darker in proportion to the level of blood present. Illustrative blood pads—once exposed to a sample containing blood—will turn from yellow color toward dark green as the level of blood in the sample increases. This is accomplished by the blood in the sample reacting with compounds in the blood reagent pad and producing a predictable color change. If, however, the color of the reagent pad doesn't change, then it is normally determined that no blood was present in the sample. Elevated levels of ascorbic acid in the sample, however, lead to a "bleaching" effect on blood reagent pads. In other words, if sufficient levels of ascorbic acid are present in the sample, the blood reagent pad will not turn from a yellow color toward dark green as when blood is present, but instead will either remain a yellow color or turn from a yellow color towards the white end of the spectrum. This lightening of the blood reagent pad is an indication that while blood may be present, the sample contains an elevated level of ascorbic acid that is masking the blood reaction. If, however, the BLO Ascorbate Algorithm is greater than the BLO Dispense Decode, then the color of the reagent pad has gotten darker and the BLO Ascorbate Algorithm will not detect the presence of ascorbic acid and will therefore indicate that problematic levels of ascorbic acid is not present 50. It should be appreciated, however, that some amount of ascorbic acid is likely to be present in the sample, despite the BLO Ascorbate Algorithm being greater than the BLO Dispense Decode.

When ascorbic acid is found 40—using one or both of the glucose pad or the blood pad, a warning can be communicated to a medical professional indicating that the test results are compromised due to the presence of elevated levels of ascorbic acid. In one example scenario, all of the actual test results can be reported to the medical professional along with the warning. In another example, some or all of the test results can be withheld.

Methods of Detecting Ascorbic Acid in a Urine Sample from a Subject

Disclosed herein are methods of, and systems for, detecting ascorbic acid in a urine sample from a subject using a non-ascorbic acid reagent pad. The disclosed methods and systems utilize test strips having reagents pads specific for glucose, blood, bilirubin, ketone, urobilinogen, nitrite, leukocyte esterase, leukocytes, albumin, and/or creatinine The disclosed methods comprise: contacting at least a portion of the urine sample with a test strip comprising a reagent pad; and detecting whether ascorbic acid is present in the urine sample by measuring an intensity of color on the reagent pad, wherein a reduction in the intensity of color on the reagent pad indicates the presence of ascorbic acid. The measuring of an intensity of color can comprise comparing a first intensity of color to a second intensity of color, wherein the first intensity of color is obtained from the reagent pad prior to the contacting step and the second intensity of color is obtained from the reagent pad after the contacting step.

The second intensity of color can be obtained about 60 seconds or more after the contacting step. In some aspects, the second intensity of color can be obtained at about 60 seconds after the contacting step. In some aspects, the second intensity of color can be obtained at about 70 seconds after the contacting step. In some aspects, the second intensity of color can be obtained at about 80 seconds after the contacting step. In some aspects, the second intensity of color can be obtained at about 90 seconds after the contacting step. In some aspects, the second intensity of color can be obtained at greater than about 90 seconds after the contacting step.

In some embodiments, the test strip comprises a glucose reagent pad, a blood reagent pad, or both a glucose reagent pad and a blood reagent pad. In such embodiments, the methods of detecting ascorbic acid in a urine sample from a subject can comprise: contacting at least a portion of the urine sample with a test strip comprising a glucose reagent pad, a blood reagent pad, or both a glucose reagent pad and a blood reagent pad; and detecting whether ascorbic acid is present in the urine sample by measuring an intensity of color on the glucose reagent pad, the blood reagent pad, or both the glucose reagent pad and the blood reagent pad, wherein a reduction in the intensity of color on the glucose reagent pad, the blood reagent pad, or both the glucose reagent pad and the blood reagent pad indicates the presence of ascorbic acid. The measuring of an intensity of color can comprise comparing a first intensity of color to a second intensity of color, wherein the first intensity of color is obtained from the glucose reagent pad, the blood reagent pad, or both the glucose reagent pad and blood reagent pad prior to the contacting step and the second intensity of color is obtained from the glucose reagent pad, the blood reagent pad, or both the glucose reagent pad and blood reagent pad after the contacting step.

The second intensity of color can be obtained about 60 seconds or more after the contacting step. In some aspects, the second intensity of color can be obtained at about 60 seconds after the contacting step. In some aspects, the second intensity of color can be obtained at about 70 seconds after the contacting step. In some aspects, the second intensity of color can be obtained at about 80 seconds after the contacting step. In some aspects, the second intensity of color can be obtained at about 90 seconds after the contacting step. In some aspects, the second intensity of color can be obtained at greater than about 90 seconds after the contacting step.

Also provided are methods of detecting ascorbic acid in a urine sample from a subject, comprising: contacting at least a portion of the urine sample with a test strip comprising a reagent pad; and detecting whether ascorbic acid is present in the urine sample by measuring an intensity of color on the reagent pad, wherein the measuring an intensity of color on the reagent pad comprises comparing a first intensity of color obtained from the reagent pad prior to the contacting step and a second intensity of color obtained from the reagent pad after the contacting step, wherein a reduction in the intensity of color on the reagent pad indicates the presence of ascorbic acid. In embodiments wherein the test strip comprises a glucose reagent pad, a blood reagent pad, or both, the measuring of an intensity of color can comprise comparing a first intensity of color to a second intensity of color, wherein a. the first intensity of color is obtained from the glucose reagent pad prior to the contacting step and the second intensity of color is obtained from the glucose reagent pad after the contacting step;

b. the first intensity of color is obtained from the blood reagent pad prior to the contacting step and the second intensity of color is obtained from the blood reagent pad after the contacting step; or c. both a and b.

The second intensity of color can be obtained about 60 seconds or more after the contacting step. In some aspects, the second intensity of color can be obtained at about 60 seconds after the contacting step. In some aspects, the second intensity of color can be obtained at about 70 seconds after the contacting step. In some aspects, the second intensity of color can be obtained at about 80 seconds after the contacting step. In some aspects, the second intensity of color can be obtained at about 90 seconds after the contacting step. In some aspects, the second intensity of color can be obtained at greater than about 90 seconds after the contacting step.

In some aspects of the disclosed methods, the first intensity of color and the second intensity of color from the reagent pad can comprise a summation of values across an RGB color system.

In some aspects, the detecting can be performed using electronics of an optical inspection apparatus. The optical inspection apparatus can include, for example, an imager to capture images (spectrophotometer, digital camera, etc.), a light source, and a computing device. As illustrated in FIG. 6, the computing device 20 can include one or more processors 22, a memory 24, an input/output 26, and a user interface (UI) 28. It is emphasized that the operation diagram depiction of the computing device 20 is exemplary and is not intended to imply a specific implementation and/or configuration. The processor 22, memory 24, input/output portion 26 and user interface 28 can be coupled together to allow communications therebetween, and can interface with the software application 30. The software application 30 may include an application programmatic interface (API). As should be appreciated, any of the above components may be distributed across one or more separate computing devices.

The memory 24 can be volatile (such as some types of RAM), non-volatile (such as ROM, flash memory, etc.), or a combination thereof, depending upon the exact configuration and type of processor 22. The computing device 20 can include additional storage (e.g., removable storage and/or non-removable storage) including, but not limited to, tape, flash memory, smart cards, CD-ROM, digital versatile disks (DVD) or other optical storage, magnetic cassettes, magnetic tape, magnetic storage or other magnetic storage devices, universal serial bus (USB) compatible memory, or any other medium which can be used to store information and which can be accessed by the computing device 20.

In various embodiments, the input/output portion 26 includes an antenna or an electronic connector for wired connection, or a combination thereof. In some implementations, input/output portion 26 can include a receiver and transmitter, transceiver or transmitter-receiver. The input/output portion 26 is capable of receiving and/or providing information pertaining to communication with a network such as, for example, the Internet. As should be appreciated, transmit and receive functionality may also be provided by one or more devices external to computing device 20. For instance, the input/output portion 20 can be in electronic communication with a receiver.

The user interface 28, which can include an input device and/or display (input device and display not shown) that allows a user to communicate with the computing device 20. The user interface 28 can include inputs that provide the ability to control the computing device 20, via, for example, buttons, soft keys, a mouse, voice actuated controls, a touch screen, movement of the computing device 20, visual cues (e.g., moving a hand in front of a camera on the computing device 20), or the like. The user interface 28 can provide outputs, including visual displays. In various configurations, the user interface 28 can include a display, a touch screen, a keyboard, a mouse, an accelerometer, a motion detector, a speaker, a microphone, a camera, or any combination thereof. It should be appreciated that the computer devices can operate via any suitable operating system, such as Android, BSD, iOS, Linux, OS X, QNX, Microsoft Windows, Windows Phone, and IBM z/OS. Furthermore, the software application can operate with any of the aforementioned operation systems.

In an exemplary embodiment of the detecting performed using electronics of an optical inspection apparatus, urine is added to a test strip containing a reagent pad. The test strip is then placed at a designated location in the imager (spectrophotometer, for example) and a start button is pressed which causes the imager to automatically process and inspect the test strip. The imager illuminates the reagent pad(s) and takes a number of reflectance readings across the RGB color system from the pad(s). The color of test strip is then determined from the relative magnitudes of red, green, and blue reflectance signals.

In some embodiments, the optical inspection apparatus can be a Clinitek Novus® Urine Analyzer.

Also provided are systems for detecting ascorbic acid in a urine sample from a subject. The disclosed systems comprise:

a memory adapted to store computer instructions;

a database; and a processor adapted to process the computer instructions to implement a method of detecting ascorbic acid in a urine sample from a subject, the method comprising: contacting at least a portion of the urine sample with a test strip comprising a reagent pad; and detecting whether ascorbic acid is present in the urine sample by measuring an intensity of color on the reagent pad, wherein a reduction in the intensity of color on the reagent pad indicates the presence of ascorbic acid.

The measuring of an intensity of color can comprise comparing a first intensity of color obtained from the reagent pad prior to the contacting step and the second intensity of color obtained from the reagent pad after the contacting step.

In some embodiments, the test strip comprises a glucose reagent pad, and the methods are performed using the glucose reagent pad. In some embodiments, the test strip comprises a blood reagent pad, and the methods are performed using the blood reagent pad. In some embodiments, the test strip comprises a glucose reagent pad and a blood reagent pad, and the methods are performed using both the glucose reagent pad and the blood reagent pad. Accordingly, in some embodiments the disclosed systems can comprise:

a memory adapted to store computer instructions;

a database; and a processor adapted to process the computer instructions to implement a method of detecting ascorbic acid in a urine sample from a subject, the method comprising: contacting at least a portion of the urine sample with a test strip comprising a glucose reagent pad, a blood reagent pad, or both; and detecting whether ascorbic acid is present in the urine sample by measuring an intensity of color on the glucose reagent pad, blood reagent pad, or both, wherein a reduction in the intensity of color on the glucose reagent pad, blood reagent pad, or both indicates the presence of ascorbic acid.

The measuring of an intensity of color can comprise comparing a first intensity of color to a second intensity of color, wherein
  a. the first intensity of color is obtained from the glucose reagent pad prior to the contacting step and the second intensity of color is obtained from the glucose reagent pad after the contacting step;
  b. the first intensity of color is obtained from the blood reagent pad prior to the contacting step and the second intensity of color is obtained from the blood reagent pad after the contacting step; or
  c. both a and b.

Further provided are non-transitory computer readable storage devices having instructions stored thereon that when executed by a processor cause the processor to implement a method of detecting ascorbic acid in a urine sample from a subject, the method comprising: contacting at least a portion of the urine sample with a test strip comprising a reagent pad; and detecting whether ascorbic acid is present in the urine sample by measuring an intensity of color on the reagent pad, wherein a reduction in the intensity of color on the reagent pad indicates the presence of ascorbic acid. The reagent pad can be a glucose reagent pad, a blood reagent pad, or both a glucose reagent pad and a blood reagent pad.

Further provided are methods of detecting ascorbic acid in a urine sample with a test strip comprising a reagent pad, the methods comprising:
  measuring, with electronics of an optical inspection apparatus, a first intensity of color from the reagent pad;
  contacting the test strip with at least a portion of the urine sample;
  measuring, with electronics of an optical inspection apparatus, a second intensity of color from the reagent pad; and
  detecting ascorbic acid in the urine sample, the detecting comprising determining a change in the intensity of color between the first intensity of color from the reagent pad and the second intensity of color from the reagent pad,
  wherein a reduction in the intensity of color on the reagent pad indicates the presence of ascorbic acid.

The test strip can comprise a glucose reagent pad, a blood reagent pad, or both. Thus, provided are methods of detecting ascorbic acid in a urine sample with a test strip comprising a glucose reagent pad, a blood reagent pad, or both a glucose reagent pad and a blood reagent pad, and comprise:
  measuring, with electronics of an optical inspection apparatus, a first intensity of color from the glucose reagent pad, a first intensity of color from the blood reagent pad, or a first intensity of color from the glucose reagent pad and a first intensity of color from the blood reagent pad;
  contacting the test strip with at least a portion of the urine sample;
  measuring, with electronics of an optical inspection apparatus, a second intensity of color from the glucose reagent pad, a second intensity of color from the blood reagent pad, or a second intensity of color from the glucose reagent pad and a second intensity of color from the blood reagent pad; and
  detecting ascorbic acid in the urine sample, the detecting comprising determining a change in the intensity of color between
  a. the first intensity of color from the glucose reagent pad and the second intensity of color from the glucose reagent pad;
  b. the first intensity of color from the blood reagent pad and the second intensity of color from the blood reagent pad; or
  c. both a and b
  wherein a reduction in the intensity of color on the glucose reagent pad, the blood reagent pad, or both the glucose reagent pad and the blood reagent pad indicates the presence of ascorbic acid.

The second intensity of color can be obtained about 60 seconds or more after the contacting step. In some aspects, the second intensity of color can be obtained at about 60 seconds after the contacting step. In some aspects, the second intensity of color can be obtained at about 70 seconds after the contacting step. In some aspects, the second intensity of color can be obtained at about 80 seconds after the contacting step. In some aspects, the second intensity of color can be obtained at about 90 seconds after the contacting step. In some aspects, the second intensity of color can be obtained at greater than about 90 seconds after the contacting step.

In some aspects of the disclosed methods, the first intensity of color and the second intensity of color from the glucose reagent pad, the blood reagent pad, or both the glucose reagent pad and blood reagent pad can comprise a summation of values across an RGB color system.

In some aspects, the optical inspection apparatus is a Clinitek Novus® Urine Analyzer.

Also provided are systems for detecting ascorbic acid in a urine sample with a test strip comprising a reagent pad, the system comprising:
  a memory adapted to store computer instructions;
  a database; and
  a processor adapted to process the computer instructions to implement a method of detecting ascorbic acid in a urine sample with a test strip comprising a reagent pad, and comprise:
    measuring, with electronics of an optical inspection apparatus, a first intensity of color from the reagent pad;
    contacting the test strip with at least a portion of the urine sample;
    measuring, with electronics of an optical inspection apparatus, a second intensity of color from the reagent pad; and
    detecting ascorbic acid in the urine sample, the detecting comprising determining a change in the intensity of color between the first intensity of color from the reagent pad and the second intensity of color from the reagent pad,
    wherein a reduction in the intensity of color on the reagent pad indicates the presence of ascorbic acid.

The test strip can comprise a glucose reagent pad, a blood reagent pad, or both. Thus, provided are systems for detecting ascorbic acid in a urine sample with a test strip comprising a glucose reagent pad, a blood reagent pad, or both a glucose reagent pad and a blood reagent pad. The disclosed systems comprise:
  a memory adapted to store computer instructions;
  a database; and
  a processor adapted to process the computer instructions to implement a method of detecting ascorbic acid in a urine sample with a test strip comprising a glucose reagent pad, a blood reagent pad, or both a glucose reagent pad and a blood reagent pad, and comprise:
    measuring, with electronics of an optical inspection apparatus, a first intensity of color from the glucose reagent pad, a first intensity of color from the blood reagent pad, or a first intensity of color from the glucose reagent pad and a first intensity of color from the blood reagent pad;

contacting the test strip with at least a portion of the urine sample;

measuring, with electronics of an optical inspection apparatus, a second intensity of color from the glucose reagent pad, a second intensity of color from the blood reagent pad, or a second intensity of color from the glucose reagent pad and a second intensity of color from the blood reagent pad; and detecting ascorbic acid in the urine sample, the detecting comprising determining a change in the intensity of color between
a. the first intensity of color from the glucose reagent pad and the second intensity of color from the glucose reagent pad;
b. the first intensity of color from the blood reagent pad and the second intensity of color from the blood reagent pad; or
c. both a and b
wherein a reduction in the intensity of color on the glucose reagent pad, the blood reagent pad, or both the glucose reagent pad and the blood reagent pad indicates the presence of ascorbic acid.

Further provided are non-transitory computer readable storage devices having instructions stored thereon that when executed by a processor cause the processor to implement a method of detecting ascorbic acid in a urine sample with a test strip comprising a reagent pad, and comprise:

measuring, with electronics of an optical inspection apparatus, a first intensity of color from the reagent pad;

contacting the test strip with at least a portion of the urine sample;

measuring, with electronics of an optical inspection apparatus, a second intensity of color from the reagent pad; and detecting ascorbic acid in the urine sample, the detecting comprising determining a change in the intensity of color between the first intensity of color from the reagent pad and the second intensity of color from the reagent pad, wherein a reduction in the intensity of color on the reagent pad indicates the presence of ascorbic acid.

The test strip can comprise a glucose reagent pad, a blood reagent pad, or both. Thus, provided are non-transitory computer readable storage devices having instructions stored thereon that when executed by a processor cause the processor to implement a method of detecting ascorbic acid in a urine sample with a test strip comprising a glucose reagent pad, a blood reagent pad, or both a glucose reagent pad and a blood reagent pad, and comprise:

measuring, with electronics of an optical inspection apparatus, a first intensity of color from the glucose reagent pad, a first intensity of color from the blood reagent pad, or a first intensity of color from the glucose reagent pad and a first intensity of color from the blood reagent pad;

contacting the test strip with at least a portion of the urine sample;

measuring, with electronics of an optical inspection apparatus, a second intensity of color from the glucose reagent pad, a second intensity of color from the blood reagent pad, or a second intensity of color from the glucose reagent pad and a second intensity of color from the blood reagent pad; and detecting ascorbic acid in the urine sample, the detecting comprising determining a change in the intensity of color between
a. the first intensity of color from the glucose reagent pad and the second intensity of color from the glucose reagent pad;
b. the first intensity of color from the blood reagent pad and the second intensity of color from the blood reagent pad; or
c. both a and b
wherein a reduction in the intensity of color on the glucose reagent pad, the blood reagent pad, or both the glucose reagent pad and the blood reagent pad indicates the presence of ascorbic acid.

EXAMPLES

The following examples are provided to further describe some of the embodiments disclosed herein. The examples are intended to illustrate, not to limit, the disclosed embodiments.

Figure 2A:
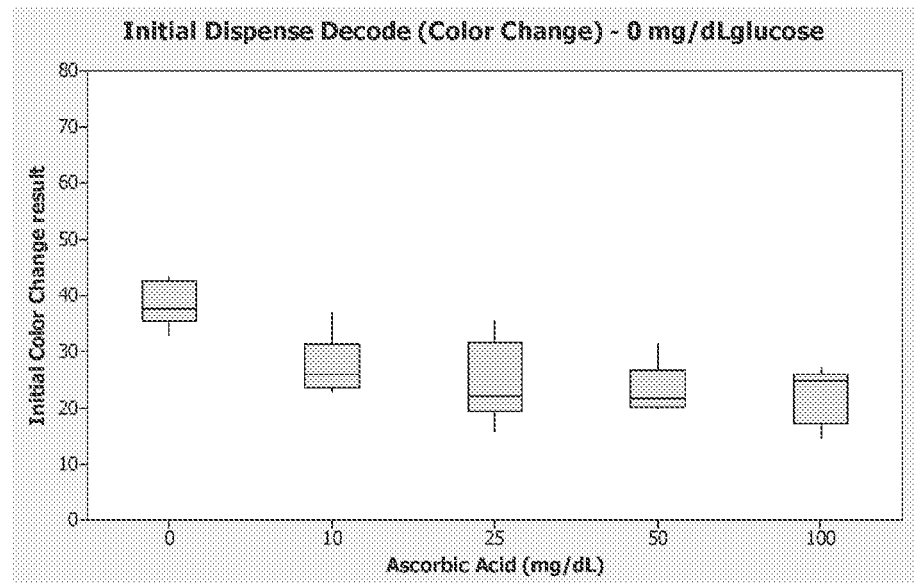
FIG. 2A and FIG. 2B illustrate a measure of the initial color change of the glucose reagent pad upon dispensing a solution having increasing amounts of ascorbic acid and (FIG. 2A) 0 mg/dL glucose or (FIG. 2B) 25 mg/dL glucose.
Figure 2B:
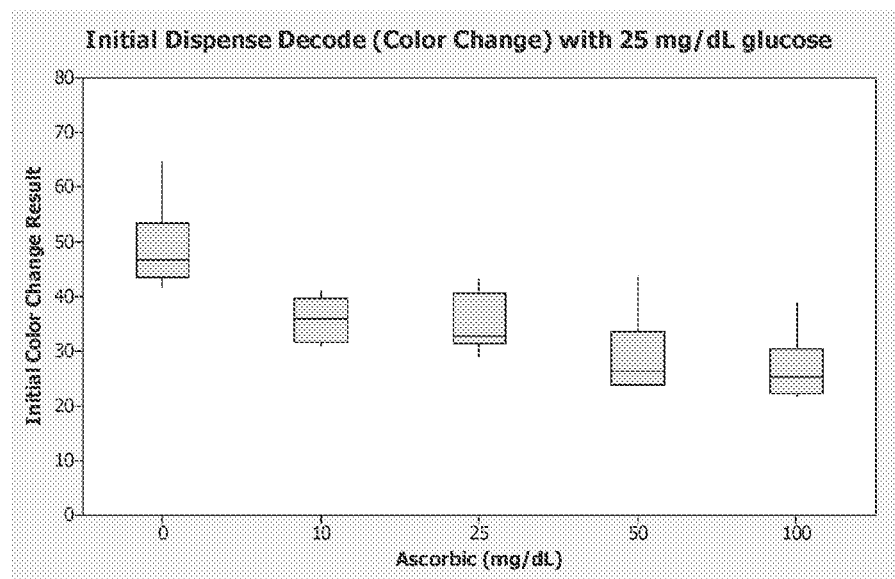

FIG. 2A and FIG. 2B show the initial color change of the glucose reagent pad immediately after dispensing a solution containing increasing amounts of ascorbic acid and (FIG. 2A) 0 mg/dL glucose or (FIG. 2B) 25 mg/dL glucose. Ascorbic acid did not influence the color change in the absence or presence of glucose immediately after dispense (i.e. within, in this example, the first 4 seconds).

Figure 3A:
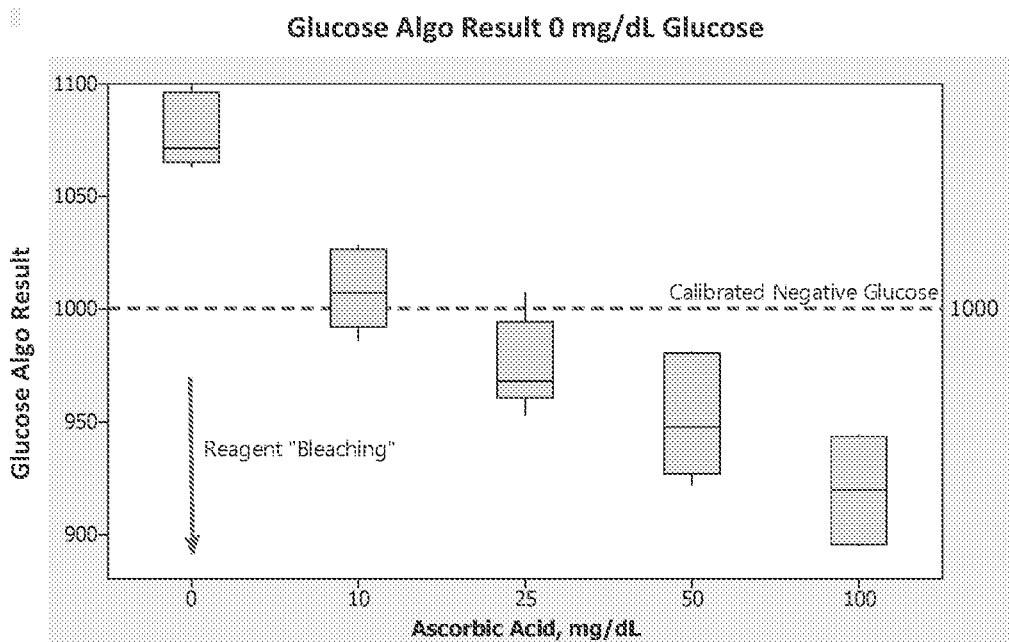
FIG. 3A and FIG. 3B illustrate the effect of ascorbic acid on the system's ability to detect glucose on the glucose reagent pad.
Figure 3B:
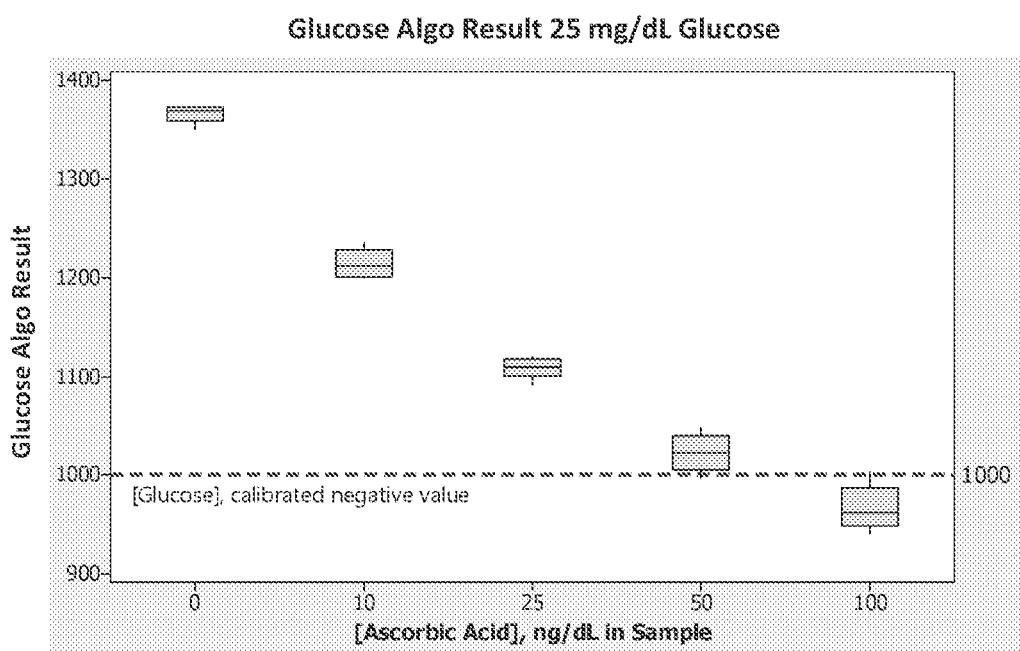

FIG. 3A and FIG. 3B illustrate the effect of ascorbic acid on the system's ability to detect glucose on the glucose reagent pad. The color measurement here was tuned to be the most sensitive to changes induced by the presence of glucose. The system was calibrated so that a glucose level of zero (i.e. no glucose in the sample) read between about a 1000 decode value and about a 1500 decode value. The dotted line at 1000 represents the absolute minimum value at which glucose can be detected (in this example, a value below 1000 should not be detected unless there is a problem with the procedure or, in this case, ascorbic acid is present). In this example, the system can report any value above 1000 depending upon the sensitivity range of the instrument. Referring to FIG. 3A: in the absence of glucose and ascorbic acid, the Glucose Algorithm value provided a value of between 1050 and 1100, which was within the negative glucose range (about 1000 to about 1500). As the amount of ascorbic acid increases, however, the Glucose Algorithm value decreases below the absolute minimum value (1000), indicating that ascorbic acid was present. Referring to FIG. 3B: in the presence of glucose but absence of ascorbic acid, the Glucose Algorithm value was between 1300 and 1400 (this value was within the negative glucose range because the machine was set to detect glucose levels at or above 50 mg/dL in this particular experiment). As the amount of ascorbic acid in the sample increases, however, the Glucose Algorithm value decreases below the absolute minimum value (1000), mimicking a sample that has no glucose. This "bleaching" effect, caused by the presence of ascorbic acid, interferes with the system's ability to detect glucose. A Glucose Algorithm value of less than 1000 indicates that the reflectance is higher than would be expected in the absence of glucose, which indicates the presence of ascorbic acid.

Figure 4A:
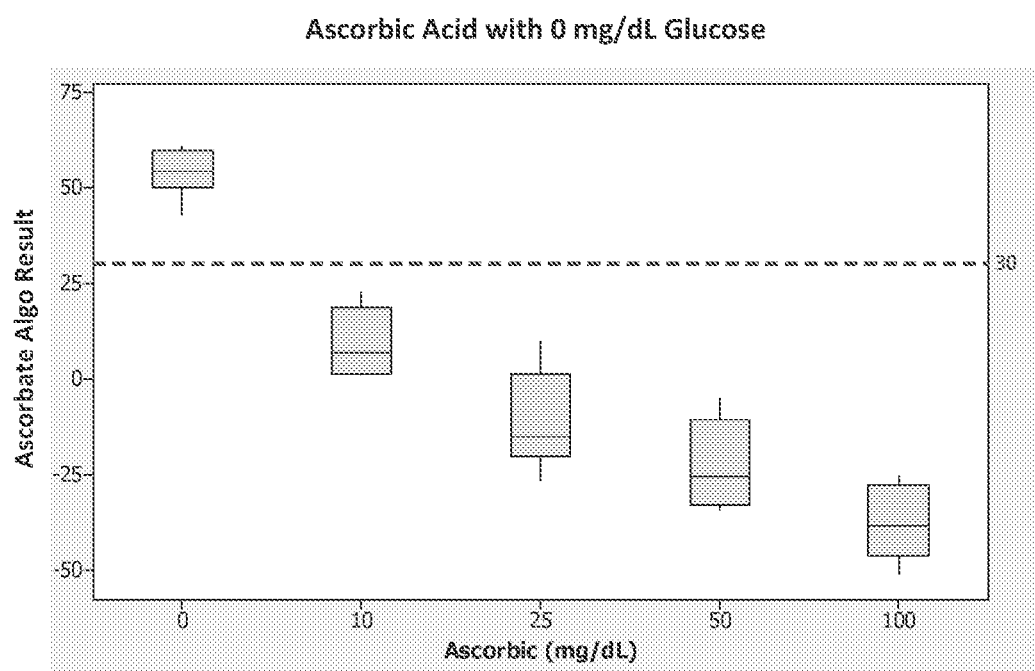
FIG. 4A and FIG. 4B illustrate the detection of ascorbic acid in a solution with (FIG. 4A) 0 mg/dL glucose and (FIG. 4B) 25 mg/dL glucose.
Figure 4B:
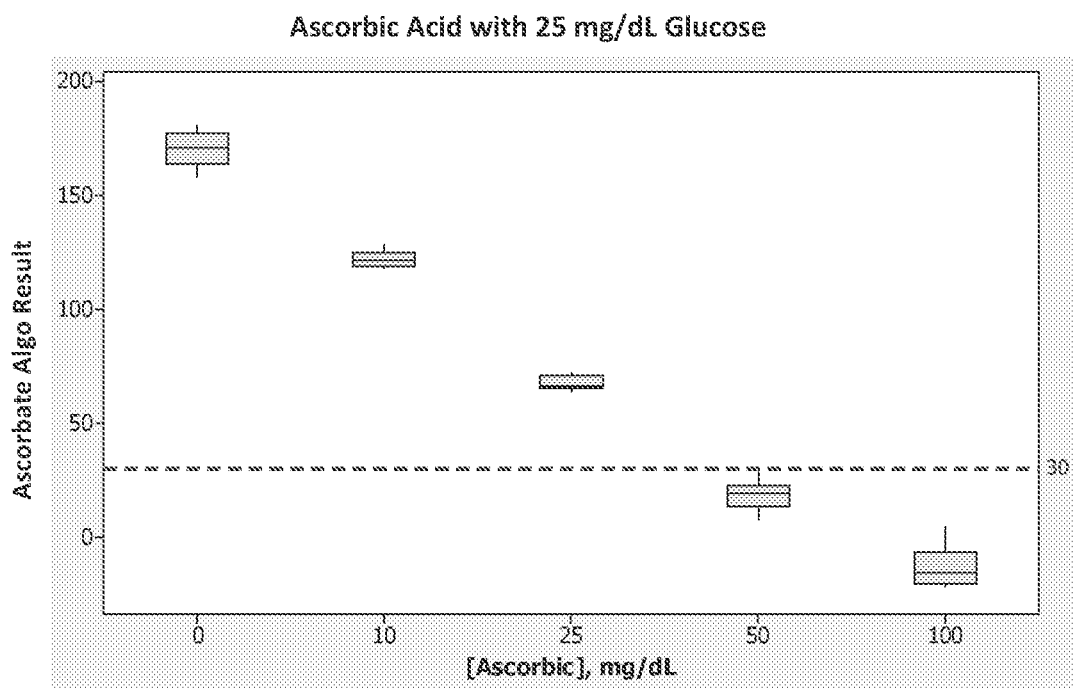

FIG. 4A and FIG. 4B illustrate the detection of ascorbic acid in a solution with (FIG. 4A) 0 mg/dL glucose and (FIG. 4B) 25 mg/dL glucose. The dotted line at 30 in each of FIG. 4A and FIG. 4B represents the detection limit for the Ascorbate Algo: an Ascorbate Algorithm value below 30 indicates the presence of ascorbic acid in the sample, whereas an Ascorbate Algorithm value above 30 indicates the absence of ascorbic acid in the sample. Referring to FIG. 4A: in the absence of glucose and ascorbic acid, the Ascorbate Algorithm value is above 30, indicating that the sample contains no ascorbic acid. As the amount of ascorbic acid increases, however, the Ascorbate Algorithm value drops below 30, indicating that ascorbic acid is present in the sample. Referring to FIG. 4B: in the presence of glucose but absence of ascorbic acid, the Ascorbate Algorithm value is above 30, indicating that the sample contains no ascorbic acid. As the amount of ascorbic acid increases, however, the Ascorbate Algorithm value drops below 30, indicating that ascorbic acid is present in the sample. Although ascorbic acid was detected in a sample containing glucose, a higher amount of ascorbic acid was required.

Figure 5:
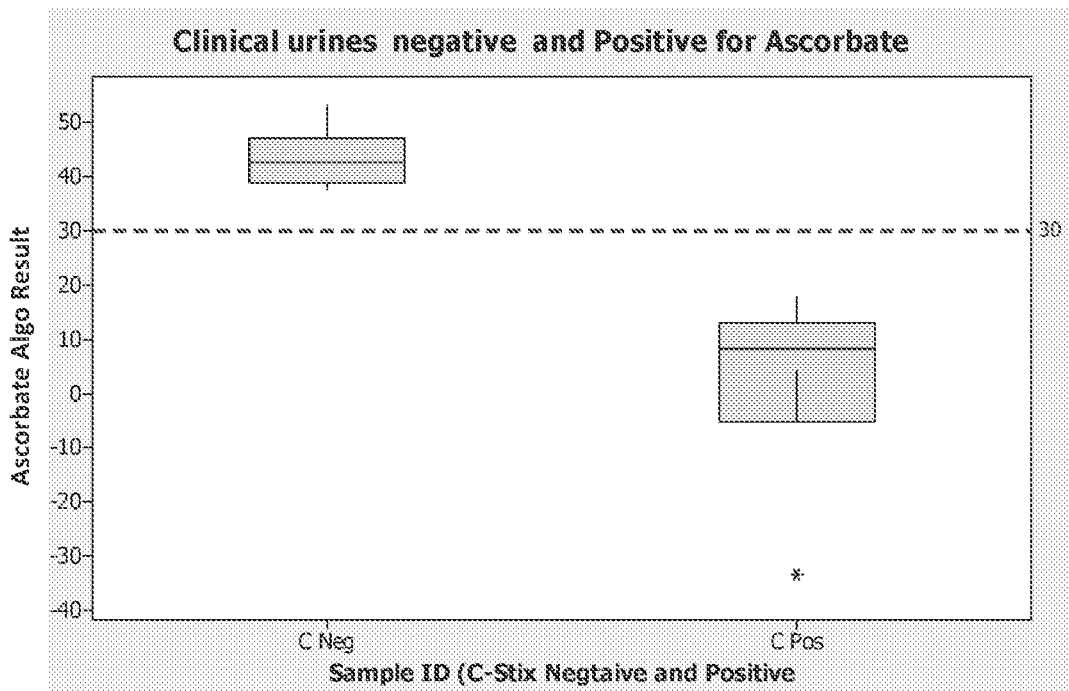
FIG. 5 illustrates the effect of ascorbic acid on the detection of glucose from a urine sample.

FIG. 5 illustrates the effect of ascorbic acid on the detection of glucose from a urine sample. To confirm the accuracy of the above algorithms, a negative control and positive control were used; a urine sample that contained no ascorbic acid and that would have provided a negative reading on a C-stix pad (reagent pad formulated to react specifically with ascorbic acid) was used as a negative control (labeled "C-Neg"), and a urine sample that contained about 30 mg/dL ascorbic acid and that would have provided a positive reading on a C-stix pad was used as a positive control (labeled "C Pos"). As shown in FIG. 5, urine samples containing no ascorbic acid ("C Neg"), when contacted to a glucose reagent pad, resulted in an Ascorbate Algorithm value above 30, indicating that no ascorbic acid was present. The urine sample containing 30 mg/dL ascorbic acid (labeled C Pos), on the other hand, when contacted to a glucose reagent pad, resulted in an Ascorbate Algorithm value below 30, indicating that ascorbic acid is present in the urine. A clear difference between the two clinical samples was observed.

The amount of ascorbic acid that can result in a negative glucose and/or reading will depend, in part, on the sensitivity of the instrumentation and reagents used, as well as the amount of glucose and/or blood that is determined to be clinically significant at the time the procedure is performed. In one exemplary implementation of the disclosed algorithms and methods, 25 mg/dL or greater of ascorbic acid in the urine can result in a negative glucose reading.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

Embodiments

The following list of embodiments is intended to complement, rather than displace or supersede, the previous descriptions.

Embodiment 1. A method of detecting ascorbic acid in a urine sample from a subject, comprising:
  contacting at least a portion of the urine sample with a test strip comprising a reagent pad; and
  detecting whether ascorbic acid is present in the urine sample by measuring an intensity of color on the reagent pad, wherein a reduction in the intensity of color on the reagent pad indicates the presence of ascorbic acid.

Embodiment 2. The method of embodiment 1, wherein the measuring of an intensity of color comprises comparing a first intensity of color to a second intensity of color, wherein the first intensity of color is obtained from the reagent pad prior to the contacting step and the second intensity of color is obtained from the reagent pad after the contacting step.

Embodiment 3. The method of embodiment 2, wherein the second intensity of color is obtained from the reagent pad at about 60 seconds or more after the contacting step.

Embodiment 4. The method of any one of the previous embodiments, wherein the test strip comprises a glucose reagent pad, a blood reagent pad, or both a glucose reagent pad and a blood reagent pad.

Embodiment 5. The method of any one of the previous embodiments, wherein the first intensity of color and the second intensity of color comprise a summation of values across an RGB color system.

Embodiment 6. The method of any one of the previous embodiments, wherein the detecting is performed using electronics of an optical inspection apparatus.

Embodiment 7. A method of detecting ascorbic acid in a urine sample with a test strip comprising a reagent pad, the method comprising:
  measuring, with electronics of an optical inspection apparatus, a first intensity of color from the reagent pad;
  contacting the test strip with at least a portion of the urine sample;
  measuring, with electronics of an optical inspection apparatus, a second intensity of color from the reagent pad; and
  detecting ascorbic acid in the urine sample, the detecting comprising determining a change in the intensity of color between the first intensity of color from the reagent pad and the second intensity of color from the reagent pad, wherein a reduction in the intensity of color on the reagent pad indicates the presence of ascorbic acid.

Embodiment 8. The method of embodiment 7, wherein the second intensity of color is obtained from the reagent pad at about 60 seconds or more after the contacting step.

Embodiment 9. The method of embodiment 7 or 8, wherein the test strip comprises a glucose reagent pad, a blood reagent pad, or both a glucose reagent pad and a blood reagent pad.

What is claimed:

1. A method of detecting ascorbic acid in a urine sample from a subject, comprising:
  contacting at least a portion of the urine sample with a test strip comprising a reagent pad including one or more compounds configured to react with an analyte in the urine sample and thereby produce a change in an intensity of color on the reagent pad;
  detecting whether the analyte is present by measuring the intensity of color on the reagent pad, wherein an increase in the intensity of color on the reagent pad after the contacting relative to before the contacting indicates a presence of the analyte; and
  detecting whether ascorbic acid is present in the urine sample by measuring the intensity of color on the reagent pad, wherein a reduction in the intensity of color on the reagent pad after the contacting relative to before the contacting indicates a presence of ascorbic acid.

2. The method of claim 1, wherein the measuring of an intensity of color comprises comparing a first intensity of color to a second intensity of color, wherein the first intensity of color is obtained from the reagent pad prior to the contacting step and the second intensity of color is obtained from the reagent pad after the contacting step.

3. The method of claim 2, wherein the second intensity of color is obtained from the reagent pad at about 60 seconds or more after the contacting step.

4. The method of claim 2, wherein the first intensity of color and the second intensity of color comprise a summation of values across an RGB color system.

5. The method of claim 1, wherein the analyte is glucose, blood, or both glucose and blood.

6. The method of claim 1, wherein the detecting is performed using electronics of an optical inspection apparatus.

7. A method of detecting ascorbic acid in a urine sample with a test strip comprising a reagent pad including one or more compounds configured to react with an analyte in the urine sample and thereby produce a change in an intensity of color on the reagent pad, the method comprising:
    measuring, with electronics of an optical inspection apparatus, a first intensity of color from the reagent pad;
    contacting the test strip with at least a portion of the urine sample;
    measuring, with the electronics of the optical inspection apparatus, a second intensity of color from the reagent pad;
    detecting the analyte in the urine sample when the first intensity of color is less than the second intensity of color; and
    detecting ascorbic acid in the urine sample, the detecting comprising determining that the second intensity of color from the reagent pad is less than the first intensity of color.

8. The method of claim 7, wherein the second intensity of color is obtained from the reagent pad at about 60 seconds or more after the contacting step.

9. The method of claim 7, wherein the analyte comprises glucose, blood, or both glucose and blood.

10. A method, comprising:
    measuring, with electronics of an optical inspection apparatus, a first intensity of color of a first reagent pad;
    contacting the first reagent pad with at least a portion of a first urine sample, wherein the first reagent pad includes one or more reagents configured to react with an analyte in the first urine sample;
    measuring, with the electronics of the optical inspection apparatus, a second intensity of color of the first reagent pad;
    detecting that the analyte is present in the first urine sample when the first intensity of color is less than the second intensity of color;
    measuring, with the electronics of the optical inspection apparatus, the first intensity of color of a second reagent pad;
    contacting the second reagent pad with at least a portion of a second urine sample, wherein the second reagent pad includes the one or more reagents configured to react with the analyte;
    measuring, with the electronics of the optical inspection apparatus, a third intensity of color of the second reagent pad;
    detecting that the analyte is not present in the second urine sample when the third intensity of color is equal to or within a threshold range of the first intensity of color;
    measuring, with the electronics of the optical inspection apparatus, the first intensity of color of a third reagent pad;
    contacting the third reagent pad with at least a portion of a third urine sample, wherein the third reagent pad includes the one or more reagents configured to react with the analyte;
    measuring, with the electronics of the optical inspection apparatus, a fourth intensity of color of the third reagent pad; and
    detecting that ascorbic acid is present in the third urine sample when the fourth intensity of color is less than the first intensity of color.

11. The method of claim 10, wherein the first reagent pad, the second reagent pad, and the third reagent pad are each a glucose reagent pad comprising one or more reagents configured to react with glucose.

12. The method of claim 10, wherein the first reagent pad, the second reagent pad, and the third reagent pad are each a blood reagent pad comprising one or more reagents configured to react with blood.

13. The method of claim 10, wherein the first reagent pad, the second reagent pad, and the third reagent pad are not ascorbic acid reagent pads.

* * * * *